United States Patent [19]

Shinkarenko

[11] Patent Number: 5,738,868
[45] Date of Patent: Apr. 14, 1998

[54] LIPOSOME COMPOSITIONS AND KITS THEREFOR

[75] Inventor: Leonid Lurya Shinkarenko, Rehovot, Israel

[73] Assignee: Lipogenics Ltd., Ariel, Israel

[21] Appl. No.: 503,662

[22] Filed: Jul. 18, 1995

[51] Int. Cl.$^6$ ............................................. A61K 9/127
[52] U.S. Cl. ..................... 424/450; 424/1.21; 424/9.321; 264/4.1; 264/4.3; 264/4.6
[58] Field of Search .................... 424/450, 1.21, 424/9.321; 264/4.1, 4.3, 4.6

[56] References Cited

FOREIGN PATENT DOCUMENTS

| | | |
|---|---|---|
| 98473 | 6/1991 | Israel. |
| 99835 | 10/1991 | Israel. |
| 57082311 | 11/1980 | Japan. |
| 2164624 | 3/1986 | United Kingdom. |

OTHER PUBLICATIONS

Kirby. in Biotechnology 11–1984, p. 979
"Methods in Enzymology", Packer, L. Editor vol 234, Part D, p. 269.
"Use of Technetium–99m–Liposomes in Tumor Imaging", Goins, B. et al, Journ Nucl Med. 1994 pp. 1491–1498.
"Liposomes Prepared from Synthetic Amphiphiles. . ." Goto, R. et al; Chem Pharm Bull pp. 1351–1354 (1989).
"Tumor Imaging with Technetium–99m–DTPA Encapsulated. . ." Oku, N et al, Nucl Med Biol vol 20, No. 4 pp. 407–412 (1993).
"Distribution of technitium–99m–Labeled Multimellar. . ." Perez–Soler, R. et al, J. Nuc Med vol 26 No. 7 (1485) pp. 743–749.
"Properties of ($^{99m}$Tc) Technetium–Labelled Liposomes. . ." Richardson, V. et al, Bioch. Soc. Trans pp. 290–291 (1977)
"Clinical Pharmacology of $^{99m}$Tc–Labeled Liposomes. . ." Lopez–Berestein et al, Cancer Res. vol. 44 pp. 375–378 (1984).
"Interaction of$^{99m}$Tc–Labeled Liposomes with Walker. . ." Todorou, D. et al Gen. Pharmac, vol. 14 No. 4 pp. 407–411 (1983).
"Biodistribution of 99m Tc Labelled Liposomes in Rabbits. . ." Ninlo, S et al. pp. 102–104.
"Effect of reticuloendothelial Blockade on Tissue" Goto R. et al. Chem Pharm Bull (1991) pp. 230–232.
"Wide dynamic range particle size analysis by DLS–SPOS" Nicoli, D.F. Int'l Spect. Lab. pp. 9A–9J (Sep. 95).

*Primary Examiner*—Gollamudi S. Kishore
*Attorney, Agent, or Firm*—Mark M. Friedman

[57] ABSTRACT

A method for preparing a radio labelled liposome, the method including the steps of at least once dehydrating and rehydrating a treated liposome to form a binding liposome, and adding a radio label to said binding liposome to form the radio labelled liposome.

8 Claims, 1 Drawing Sheet

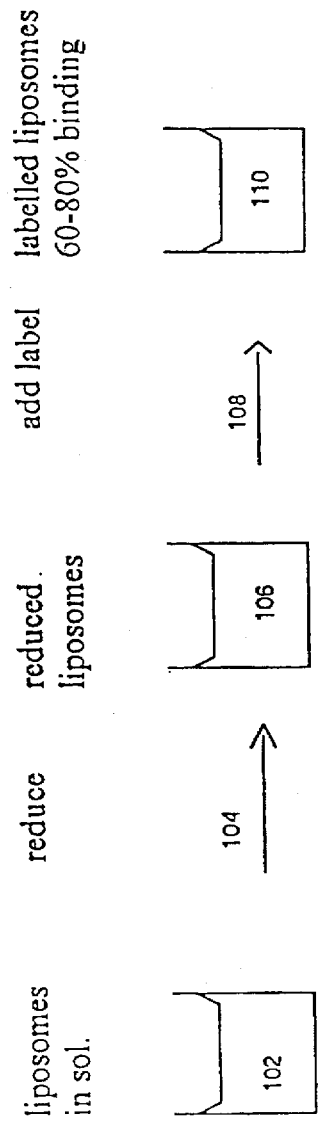
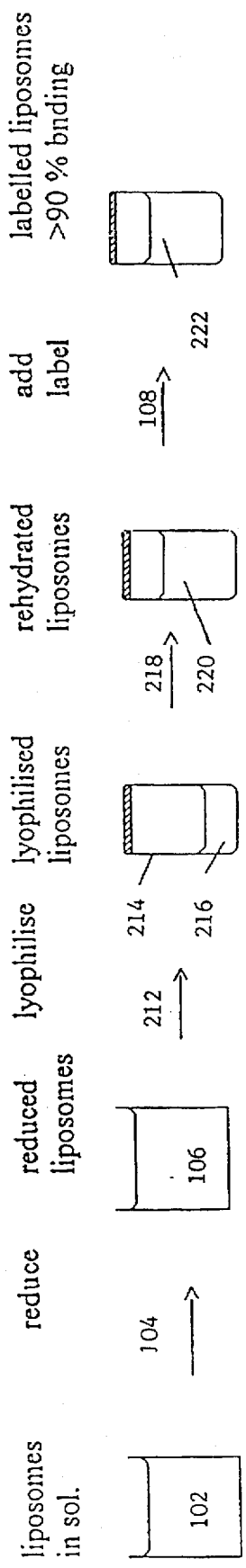

5,738,868

LIPOSOME COMPOSITIONS AND KITS THEREFOR

FIELD AND BACKGROUND OF THE INVENTION

The present invention relates to radio-labelled liposome compositions and, more particularly, to lyophilized liposome compositions suitable for radio-labelling.

Liposomes are spherical structures composed of bilayers of ampiphiles, a special class of surface active molecules, which are characterized by having a hydrophilic (water-soluble) and a hydrophobic (water-insoluble) group on the same molecule. Liposomes can be large or small, and be composed from one to several of these bilayers.

Liposomes can be prepared by a variety of methods well known in the art which include, by way of example, methods using natural ampiphiles, such as phospholipids, as well as methods such as that of Goto et al. set forth in Chem. Pharm. Bull. 37 (5) 1351–1354 (1989) for preparing artificial liposomes.

Liposomes provide an effective means for selectively delivering a variety of agents, such as diagnostic agents and drugs, throughout a body.

Liposome-encapsulated agents often have biodistributions and efficiencies which differ greatly from the free agents. In particular, it is often desired to provide drugs through inhalation. The rapid systemic uptake of an agent from the site of administration in the respiratory tract can be eliminated or greatly reduced by administering it in a predominantly liposome-encapsulated form, leading to reduced toxicity and improved therapeutic action over an extended period of time.

Liposomes labelled by radioactive agents are employed to diagnostically image tumors, abscesses, ischemic and infected regions and other inflammatory sites, such as rheumatoid arthritis.

Two basic approaches used to label liposomes for such diagnostic imaging purposes have been described in the publication "A Simple Method for Producing Technetium-99m-labelled Liposome which is Stable in Vivo" by Phillips et al, Nucl. Med. Biol. Vol. 19, No. 5. pp. 539–547. 1992. One approach involves the entrapment of radio-nuclotides during the initial hydration of the lipids in an aqueous phase. This approach is not convenient because the radioactive agent must be used immediately following manufacture and cannot be stored. This approach also has a disadvantage of a low encapsulation efficiency of below 30%.

The second more conventional approach is to label preformed liposomes with a radio-active diagnostic agent immediately prior to imaging. This method is ideally suited for clinical applications as the liposomes can be manufactured off-site and distributed to the clinician in kit form. However, when labelling is carried out by this conventional method, the labelling efficiency is only between about 60 and 80%.

At present Technetium (99 mTc) is by far the most widely used radio-active diagnostic agent. Attempts to label preformed liposomes with Technetium using this approach have produced similarly variable and inconsistent results.

The most common method uses stannous chloride ($SnCl_2$) as a reducing agent which, when applied together with Technetium, binds the Technetium to the liposome membrane.

The conventional prior art method of preparing radio-labelled liposomes is illustrated schematically in FIG. 1.

According to this method, stannous chloride 104, is added to a suspension 102 of liposomes, to form treated liposomes 106. A portion of the stannous chloride is bound up with the liposomes and a portion remains free in the suspension. A radio-label 108, such as Technetium, is added to treated liposomes 106 to provide a radio-labelled liposome 110, binding with labelling efficiencies averaging between about 80% to 60% efficiency, and often as low as 50%!

Various attempts have been made to provide a highly labelled Technetium liposome. The method described in the above article by Phillips describes the use of the lipophilic chelator hexamethylpropylenamine oxide (HMPAO) in addition to stannous chloride.

While the presence of HMPAO appears to improve the efficiency of labelling, HMPAO is expensive. Furthermore, liposomes must be prepared encapsulating glutathione adding to the cost of preparing radio-labelled liposomes.

It is believed, the mason for lowered labelling efficiencies of these conventional labelling methods is, that free stannous chloride in the liposome suspension binds a portion of the Technetium, but does not associate with the liposome.

There is thus a widely recognized need for a method for inexpensively preparing a liposome that can be labelled with high efficiency, and it would be highly advantageous to be able to store such a prepared liposome in such a way that it can easily be labelled.

SUMMARY OF THE INVENTION

According to the present invention there is provided a method for preparing a radio-labelled liposome including the step of adding a radio-label to a treated liposome substantially in the absence of free binding agent, to form a liposome binding with at least 90% of the added label.

There is also provided in accordance with the present invention a method for preparing a radio-labelled liposome including the steps of: dehydrating a treated liposome, rehydrating the dehydrated liposome, to form a binding liposome; and adding a radio-label to the binding liposome, to form a liposome binding at least 90% of the added label.

According to further features in preferred embodiments of the invention described below, the method further includes the steps of dehydrating a treated liposome in suspension and resuspending the dehydrated suspension into a binding liposome suspension prior to radio-labelling.

According to one preferred embodiment of the invention described below, the method of preparing a binding liposome is performed under vacuum. According to a further embodiment, the step of dehydrating a treated liposome is performed under vacuum. According to yet a further embodiment of the same invention, the steps of rehydrating the dehydrated liposome, and adding a radio-label to the rehydrated binding liposome are performed under vacuum.

There is also provided in accordance with a preferred embodiment of the present invention, a kit for preparing a radio-labelled liposome, the kit comprising a binding liposome. According to a preferred embodiment of the present invention, the kit further includes a stability agent.

According to further features in preferred embodiments of the invention described below, the step of dehydration includes lyophilization to form a lyophilized powder.

There is further provided in accordance with the present invention, a stable dehydrated powder of a treated liposome.

There is still further provided in accordance with a preferred embodiment of the present invention, a kit for preparing a radio-labelled liposome, the kit comprising a lyophilized liposome pre-treated with a reducing agent. In a more preferred embodiment of the present invention, there is provided a kit for preparing a radio-labelled liposome the kit further comprising lyophilized liposomes pre-treated with a reducing agent together with a stability agent.

The present invention successfully addresses the shortcomings of the presently known configurations by providing a novel method for preparing a liposome that can be labelled with a high efficiency, above 80%, and preferably about 90%, more preferably at least about 95%, and most optimally about 98%.

BRIEF DESCRIPTION OF THE DRAWINGS

The invention is herein described, by way of example only, with reference to the accompanying drawings, wherein:

FIG. 1 is a schematic illustration of the method of preparing a radio-labelled liposome according to the prior art; and FIG. 2 is a schematic illustration of the method of preparing a radio-labelled liposome according to one embodiment of the present invention.

DESCRIPTION OF THE PREFERRED EMBODIMENTS

The present invention relates to a method for preparing a radio-labelled liposome, in which a radio-labelling agent is bound with between at least about 90% to about 98% efficiency, and a radio-labelled liposome prepared by this method. This invention also relates to a kit for preparing a binding liposome, as defined herein below, for labelling with a radio agent at the time of use.

It is a particular feature of the invention that stable dehydrated powders of the prepared liposome can be prepared which can be stored for relatively long periods of time prior to rehydration and radio-labelling.

The principles and operation of preparing a radio-labelled liposome according to the present invention may be better understood with reference to the drawings, the accompanying description and non-limiting example.

The method of the present invention is illustrated schematically in FIG. 2. A suspension 102 of liposomes is prepared, as known. Preferably, liposome suspension 102 is prepared by the method of injecting water into a lipid dissolved in an organic solvent. A reducing agent 104, such as stannous chloride, is added to the liposome suspension 102, to form treated liposomes 106. Liposomes 106 are dehydrated to form dehydrated liposome 216. Dehydrated liposome 216 is rehydrated, to form a binding liposome 220. A radio-label 108, such as Technetium is added to binding liposome 220 to provide a radio- labelled liposome 222, binding with at least about 90% to about 92% efficiency.

Preferably liposomes 102 are prepared from an organic solution containing a plurality of ampiphiles. Suitable organic solvents includes chloroform, ether, low alkyl alcohols and the like. It is preferable that the process of manufacturing liposomes 102 be carried out using a one line process under vacuum. It is appreciated that the presence of a vacuum aids evaporation of the organic solvent during liposome formation. It is preferable that liposome formation must be performed at temperatures between 20° C. and 40° C.

It is preferable that naturally occurring ampiphiles similar to those appearing in the human body be used. For lung diagnostic applications, suitable ampiphiles include Dilauryl phosphatidil choline (DLPC), Dimyristol phosphatidil choline (DMPC), Dipalmitoyl phosphatidil choline (DPPC), Distereoyl phosphatidil choline (DSPC) and dioleoyl phosphatidil choline, most preferably dioleoyl phosphatidil choline. Alternatively, other synthetic ampiphiles may be used. Both DLPC and DPPC are manufactured by Avanti Polar Lipids Inc., USA. Avanti further manufactures a wide variety of naturally occurring and synthetic ampiphiles suitable for alternative applications.

Alternatively, the ampiphiles may be modified by binding a selected immuno-globulin in order to produce radio-labelled liposomes that may be targeted to a specific location, such as a rumor site. It is appreciated that such targeted radio-labelled liposomes may be used to diagnose the presence of such a tumor. It is further appreciated that radio-labelled liposomes may be produced that carry active pharmaceutical agents.

Reducing agent 104 may be any reducing agent or means of reducing the liposomes so as to provide treated liposomes. Preferably reducing agent 104 is stannous chloride.

Alternatively, for the purposes of the present invention and claims, a treated liposome includes any liposome that has been treated in such a way by other forms of binding agent or electro-chemical treatment that liposome will bind to an added radio-label.

Reducing agent 104 is preferably added in aqueous solution to liposome suspension 102 under vacuum, increasing the amount of added reducing agent that binds to the liposomes. To achieve efficient binding, between about 19 and about 50 micrograms of stannous chloride is used for per gram of lipid. It is preferable that 26 micrograms of stannous chloride is used for per gram of lipid.

Dehydration of treated liposomes 106 can be carried out in any fashion. Preferably, dehydration is carried out by freeze dry lyophilization. The treated liposomes are first frozen using liquid nitrogen. The frozen liposomes are then subjected to a high vacuum so that the frozen water is vaporized in the vacuum without melting, leaving the liposome in a dry state. Preferably the steps of dehydration and rehydration are repeated at least once.

According to the present method liposomes 216, lyophilized at least once bind with between about 90% to about 95% efficiency, and with an average binding efficiency of 92%. Liposomes 216, when lyophilized a second time have been found to consistently bind to Technetium with between about 92% to about 98% efficiency and with an average binding efficiency between about 95% to about 96%. Preferably the lyophilized liposomes 216 are in powder form.

Prior to radio labelling, the dehydrated liposomes are rehydrated by any conventional method to form rehydrated liposome 220 in suspension.

For the purposes of the specification and claims, a liposome treated with reducing agent, dehydrated and rehydrated to form liposome 220 is referred to as a binding liposome. Binding liposomes 220 are labelled by the addition of Technetium preferably under vacuum in the absence of oxygen, prior to delivery.

It is believed, without any way limiting the scope of the present invention, that the process of dehydration and rehydration serves to remove most of the free reducing agent from the liposome suspension and to associate it with the liposomes, leaving almost no free reducing agent.

It is a feature of the invention that the present method can be used to achieve high binding efficiency when labelling with other clinical radio nucleotides including but not limited to Gallium-67 ($^{67}$Ga), Indium-115 ($^{111}$In), Iodine-125 ($^{125}$I), Iodine-131 ($^{131}$I), Cobalt-57 ($^{57}$Co) and the like.

The addition of Technetium to binding liposomes 220 forms radio-labelled liposomes 222 binding with between about 90% to about 95% efficiency, and usually with an average binding efficiency of about 92%.

A non-limiting example of preparation of a radio-labelled liposome according to the present invention follows.

EXAMPLE 1

10 ml of 10 mg/ml DLPC dissolved in chloroform was introduced into a 100 ml Erlemeyer flask. 10 ml of degassed distilled water was added to the resulting mixture. A TEFLON coated magnet for a magnetic stirrer was placed inside the flask. The flask was closed with a connector fore tube and the air evacuated by a dry vacuum pump until the chloroform started to boil. The flask was then closed to maintain its current pressure, and the mixture vigorously stirred at room temperature for approximately 10 minutes until a fine lipid suspension formed.

Additional chloroform was removed by stirring the lipid suspension under vacuum at a reduced speed. During the chloroform evaporation a gel formed. While continuing to stir and as more chloroform evaporated, the gel converted into a liposome suspension. The temperature of the gel was elevated to 37° C., and stirred under vacuum for a further 15 minutes at a minimum speed, until traces of chloroform were removed. Additional degassed distilled water was added to the liposome suspension to bring its volume up to 10 ml.

A 1.0 mg/ml Stannous chloride solution was prepared by dissolving 10 mg of Stannous chloride in 10 ml of distilled water under vacuum.

Under vacuum, 5 ml of the Stannous chloride solution was introduced into the Erlenmeyer flask containing the liposome suspension, and the resulting mixture stirred vigorously at room temperature for 10 minutes. 5.25 ml of the resulting suspension of Stannous chloride treated liposomes were removed by aliquot from the flask and transferred to a vial.

The contents of the vial were then frozen by immersing the vial into liquid nitrogen. The frozen contents of the vile were dried by a Christ Alpha 1-2 lyophilizer manufactured by Christ of Germany. The lyophilizer dried the vial for approximately 16 hours under a 0.035 mBar vacuum to produce 5 mg of lyophilized liposomes. The vial containing the lyophilized liposomes was then sealed under vacuum at 0.035 mBar pressure with an air tight resin cap.

1 to 2 ml of hospital standard apirogenic 0.9% NaCl solution was injected into a vial storing 5 mg of treated liposome powder under vacuum. 30 mCi of Na-pertechnetate was added and the resultant mixture incubated at room temperature for between about 10 to 30 minutes. Between 90 and 95% binding efficiency was obtained.

It is a particular feature of the present invention that lyophilized liposomes 216 can be stored as a powder prior to labelling. It will be appreciated that storage of the powder under vacuum is preferred in order to ensure long term stability of the liposome 216. It is further appreciated that predetermined selected amounts of liposome 216 can be stored under vacuum in sealed vials to be used by a technician at the time of labelling.

Typically between 1 to 5 mg of liposome 216 will be stored in a sealed vial 214 under partial or full vacuum. Use of vial 214 containing a selected amount of liposome 216 has the advantage that little or no calculation is required by the clinician in order to prepare selected amounts of labelled liposome 222 for use.

It is a further advantage of the present method that substantially lower levels of free Staunous chloride is present in labelled liposome 222.

There is also provided in accordance with the present invention a kit for preparing radio-labelled liposome 222. The kit includes a predetermined quantity of treated liposome stored in a vial. The liposome may stored in a dehydrated form or in a hydrated form, preferably under vacuum.

Preferably the kit also includes stabilizing and/or anti-oxidizing agents which prevent the liposomes from either braking down, changing size or oxidizing. Suitable naturally occurring anti-oxidants include but are not limited to vitamin E, vitamin C, vitamin A, Beta-carotene, glutathione, flavonoids, alpha-Lipoic acid, various quinones such as Ubiquinones, ubiquinols, alpha-Tocopherol, alpha-Tocotrienol and the like. Alternatively, synthetic antioxidants may be used.

More preferably the kit also includes a suitable cryoprotector which prevents change to the liposome's morphology during freeze drying, storing and reconstitution. Suitable cryo-protectors include but are not limited to sugars such as mannitol, sucrose, dextrose, and the like. Alternatively Poly Ethylene Glycol (PEG) may be also used. The labelled liposome solution is suitable for delivery to the respiratory tract by inhalation from a liquid solution using a nebuliser. Alternatively the solution can be injected directly into the blood system. Furthermore, the solution can be injected either subcutaneously or intra-muscularly into a subject.

It is a particular feature of the present method, that diagnostic inhalation tests performed on healthy test subjects show that about ⅓ the quantity of radio-labelling agent was required as contrasted with radio-labelled liposomes formed by conventional methods of formulation.

Thus according to the present invention, a typical 3 ml dose of radio-labelled liposome solution contains only 10 mCi of radio-active material, as opposed to 30 mCi in conventional formulations.

It is believed, without in anyway limiting the scope of the present invention, that this is due to high binding efficiency performed substantially in the absence of free binding agent.

Thus one third the concentration of radioactive material suffices to give results of the same radiographic quality, saving both time and material during each radiographic test.

While the invention has been described with respect to a limited number of embodiments, it will be appreciated that many variations, modifications and other applications of the invention may be made.

What is claimed is:

1. A method for preparing a radio labelled liposome, the method comprising the steps of:
   (a) adding a reducing agent to a liposome under vacuum to form a treated liposome;
   (b) dehydrating under vacuum said treated liposome, to form a dehydrated liposome;
   rehydrating under vacuum said dehydrated liposome, to form a rehydrated liposome; and
   (d) adding a radio label to said rehydrated liposome under vacuum, to form a radio labelled liposome binding at least about 90% of an added radio label.

2. A method for preparing a radio labelled liposome, the method comprising the steps of:

(a) adding a reducing agent to a liposome under vacuum to form a treated liposome;

(b) dehydrating said treated liposome under vacuum, to form a dehydrated liposome;

(c) rehydrating said dehydrated liposome under vacuum, to form a rehydrated liposome; and (d) adding a radio label to said rehydrated lipsome under vacuum, to form the radio labelled liposome.

3. The method of claim 2, wherein said liposome is contained in a liposome suspension.

4. A method for preparing a radio labelled liposome, the method comprising the steps of:

(a) adding stannous chloride to a liposome under vacuum to form a treated liposome;

(b) dehydrating said treated liposome under vacuum, to form a dehydrated liposome;

(c) rehydrating said dehydrated liposome under vacuum, to form a rehydrated liposome; and (d) adding a radio label to said rehydrated lipsome under vacuum, to form the radio labelled liposome.

5. The method of claim 2, wherein said steps of dehydrating and rehydrating are repeated prior to said step of adding said radio label.

6. The method of claim 5, wherein said step of dehydrating includes lyophilization.

7. The method of claim 2, wherein said reducing agent is stannous chloride.

8. The method of claim 2, wherein said liposome is formed from an ampiphile selected from the group consisting of dilauryl phosphatidyl choline, dimyristol phosphatidyl choline, dipalmitoyl phosphatidyl choline, dioleoyl phosphatidylcholine and distereoyl phosphatidyl choline.

* * * * *